(12) United States Patent
Werlich

(10) Patent No.: US 10,815,589 B2
(45) Date of Patent: Oct. 27, 2020

(54) COTTON MIXES HOMOGENIZATION WITHOUT CATEGORIZING BALES IN INVENTORY

(71) Applicant: WW SISTEMAS INTELIGENTES LTDA-ME, Afredo Wagner-SC (BR)

(72) Inventor: Jaison Werlich, Alfredo Wagner-SC (BR)

(73) Assignee: WW SYSTEMS LTDA, Estreito/SC (BR)

( * ) Notice: Subject to any disclaimer, the term of this patent is extended or adjusted under 35 U.S.C. 154(b) by 146 days.

(21) Appl. No.: 15/948,955

(22) Filed: Apr. 9, 2018

(65) Prior Publication Data

US 2018/0237958 A1 Aug. 23, 2018

Related U.S. Application Data

(63) Continuation-in-part of application No. PCT/BR2015/050177, filed on Oct. 9, 2015.

(51) Int. Cl.
*D01G 99/00* (2010.01)
*D01G 13/00* (2006.01)
*G01N 33/36* (2006.01)
*G01N 15/14* (2006.01)

(52) U.S. Cl.
CPC ............. *D01G 99/00* (2013.01); *D01G 13/00* (2013.01); *G01N 33/362* (2013.01); *D10B 2201/02* (2013.01); *G01N 2015/1486* (2013.01)

(58) Field of Classification Search
CPC ...... D01G 99/00; D01G 5/00; D01G 7/00–14; D01G 9/00–22; D01G 15/40; D01G 21/00; D01G 23/00; D01G 13/00; G01N 33/36; G01N 33/362; G01N 2015/1486; G01N 2015/1488; G01N 2015/149; D10B 2201/02
See application file for complete search history.

(56) References Cited

U.S. PATENT DOCUMENTS

| | | | | |
|---|---|---|---|---|
| 1,927,677 A | * | 9/1933 | Bennington | B65G 1/0407 187/244 |
| 3,166,797 A | * | 1/1965 | Mayer, Jr. | D01G 7/04 19/81 |
| 3,347,102 A | * | 10/1967 | Phillips | G01N 1/08 73/863.81 |

(Continued)

*Primary Examiner* — Ismael Izaguirre
(74) *Attorney, Agent, or Firm* — Muncy, Geissler, Olds & Lowe, P.C.

(57) ABSTRACT

Describes a method for cotton mixes homogenization without categorizing bales in inventory, i.e., with no separation of bales into classes, whose main objective is to eliminate the large variability of cotton fiber quality for the spinning process resulted from data input concerning the quality of the mixes and inventories. With this method no categorization in inventory is required and more than 20 quality parameters can be controlled with no impact on the physical inventory management. The method is intended to solve problems in the production of cotton fibers relative to the variability among mixes, variability among the loads of the mixes and variability in the laydown of the bales resulting in cotton fiber with higher quality, as well this method presents an optimized logistics in the warehouse.

13 Claims, 3 Drawing Sheets

(56) References Cited

U.S. PATENT DOCUMENTS

| | | | | |
|---|---|---|---|---|
| 5,038,438 A | * | 8/1991 | Gunter | D01G 21/00 19/200 |
| 5,515,577 A | * | 5/1996 | Pinto | D01G 7/10 19/80 R |
| 5,768,750 A | * | 6/1998 | Williams | D01G 7/08 19/80 R |
| 5,805,452 A | * | 9/1998 | Anthony | D01G 31/006 700/142 |
| 6,408,221 B1 | * | 6/2002 | Demuth | D01G 7/00 700/130 |
| 2002/0108216 A1 | * | 8/2002 | Foster | D01G 13/00 19/145.5 |

* cited by examiner

Mix Inventory Calculation

1 First the bales quantity, the quality and the factor for each group of piles (GP) are calculated separately as follows:

Bales Qty GP = 0
Quality GP = 0
Index = 1

While Index <= qty of de piles in GP
Begin
  Bales Qty GP = Bales Qty GP + Bales Qty in Pile[Index]
  Quality GP = Quality GP + (Bales Qty in Pile[Index]* Quality Pile [Index])
  Index = Index 1
end;

Quality GP = Quality GP / Bales Qty GP;
Factor GP = Bales Qty GP / % in the mix GP

2 From the calculation of each group of piles (GP) mix inventory of the production line is calculated:

- Calculation of the bales qty of the mix inventory:
  Qty Bales of the Mix Inventory = 0;
  Index = 1;
  While Index <= Qty GPs
  begin
    Qty Bales of the Mix Inventory = Qty Bales of the Mix Inventory +(Qty GP[Index]* Factor GP[Index]/ Greatest Factor GP)
    Index = Index +1;
  End;

- Calculation of the quality inventor of the mix:
  Quality of the Mix Inventor= 0;
  Index = 1;
  While Index <= Qty GPs
  begin
    Quality of the Mix Inventory = Quality of the Mix Inventory + (Quality GP[Indice] * % in the mix GP / 100);
    Index = Index + 1;
  End;

Mix Inventory Calculation
Example

Pile 01
Bales qty = 90
MIC = 4.05
GP = A

Pile 02
Bales qty = 90
MIC = 3.95
GP = A

Group of the Piles (GP) = A
% in the mix = 60%

Group of the piles (GP) inventory = A
Bales Qty GP A = (90 + 90);
Bales Qty GP A = 180 bales;

Quality Micronaire GP A= (4,05*90)+(3,95*90) = 720;
Quality Micronaire GP A = 720/180;
Quality Micronaire GP=4,00

Factor GP = Bales Qty GP A / % in the mix GP A;
Factor GP = 180/60;
Factor GP = 3;

Pile 03
Bales qty = 80
MIC = 3.65
GP = B

Pile 04
Bales qty = 80
MIC = 3.55
GP = B

Group of the Piles (GP) = B
% in the mix = 40%

Group of the piles (GP) inventory = B
Bales Qty GP B = (80 + 80);
Bales Qty GP B = 160 bales;

Quality Micronaire GP B = ((3,65*80)+(3,55*80)) = 576;
Quality Micronaire GP B = 576/160;
Quality Micronaire GP B =3,60

Factor GP = Bales Qty GP B / % in the mix GP B;
Factor GP = 160/40;
Factor GP = 4;

FIG. 3

COTTON MIXES HOMOGENIZATION WITHOUT CATEGORIZING BALES IN INVENTORY

It is a method of cotton mixes homogenization without categorizing bales in inventory (categories). Basically the method aims to eliminate the variability among the mixes of one production line along the spinning process which consequently ensures higher quality in cotton fiber with considerable operational work reduction when laying bales down in inventory. The method herein revealed can be applied manually with use of manual or digital spreadsheets, such as Excel, or using computer program.

Cotton for yarn production is delivered at plants grouped in different trucks containing individually about 130 bales which—each truck or cotton lot—hereafter is denominated "invoice". When downloading the cotton, a fractioned sample is removed of each bale, and sent to classification, where quality will be obtained, in some cases, bales have already the quality data report provided by the cotton producer, thus there is no need to remove the samples. After obtaining the data of quality of each bale, companies which aim better quality in the spinning process, categorize the bales according to the quality of the cotton, i.e. according to their physical and chemical characteristics they categorize [the bales] in different piles that are denominated classes. This method requires great operational work as each bale should be reallocated to the class which will be part considering its quality range. This form of work procedure considers that all the bales in a class have the same quality range, which can result bales with quality discrepancy, since each bale of the class has different qualities. Once the classes are defined, the quantity of each bale is set to be mixed to obtain the desired characteristics of the yarn. The definition of how many bales will be obtained in each class is performed manually by experienced technicians and varies according to each production line. This "recipe" made by the technician is called "mix load" and from it various mixes are made. Either the variation in quality among the bales of the same class or the variation of the mixes are considered, in such case the margin of error between the aimed yarn and the yarn achieved is significant. Given that the bales have different quality values from each other, there will be three stages in which there is great variation in the quality spinning.

1 Variability among mixes: Given quality changes in the piles, usually there is considerable variation between the quality of the ongoing mix and the following one.

2 Variability among different sets of laydown: As the bales are obtained randomly from each pile and there is variation in the quality of the bales grouped in the same pile, each time a new laydown set is picked up, there is variation in the quality of the cotton among different sets of laydown.

3 Variability inside the laydown set in the opening line: As each bale of the laydown set has different quality ranges, the inappropriate laydown in the opening line causes variation in yarn production of a same laydown set.

Currently there are various patents for picking areas as well as cotton yarn production regarding spinning, such as PI0602724-5, registered by the same inventor as follows "cotton mixes homogenization" which is a method with the same objective, however it has limitations regarding the method revealed in this report, once the bales should be categorized in inventory and it limits the quality control in a maximum of 5 parameters. The control of more than 5 parameters (characteristics) would generate a huge amount of piles, which makes the physical management of the inventory unfeasible. Opposing the method revealed in this report which no categorization in inventory is required and where you can control more than 20 quality parameters with no impact on the physical inventory management. Comparatively the method described in the PI06002724-5 reports fewer features to control the quality of mixes and does not produce results—in what concerns yarn quality—as efficiently as this method revealed in this report.

Patent documents U.S. Pat. Nos. 5,210,909A, 5,282,141A and 5,025,533A are still in the state of the art.

The method described in patent processes U.S. Pat. Nos. 5,210,909A, 5,282,141A and 5,025,533A, consists of a mechanized solution for making cotton mixes. This process occurs with the cotton bales already physically disposed on the production lines and depends on specific electronic equipment both to measure the values of the fiber characteristics and the consumption of the bales, such as arms and conveyor belts. This method requires that a mixture of cotton bales be pre-elaborated and only then can be put into practice.

Although both methods address the same theme, the method disclosed in this report is still in the quality planning and choice of the bales that will comprise the mix step, a step prior to that described in the patent process U.S. Pat. No. 5,210,909A which uses completely different mechanisms, resources and methodologies.

The method of picking cotton bales to obtain the load of the mix (laydown set), described in this report, works with the data on the quality of cotton contained in stored bales, then performs the various functions such as picking bales that will be the load of each mix and quality variability optimization among mixes. Basically, it is designed to homogenize cotton mixes by combining the data of the bales in inventories. The method allows, first, to work with the optimization of variability among mixes, performing the planning, the premix and the selection of bales of each mix (laydown set) through cotton quality data in inventory, specifying values and percentage of weight of each feature. Finally, the method also enables an organization to be made in the arrangement of bales in the opening line of the laydown set, based on an already existing data in the spreadsheets or in a computer program, allocating the bale, dividing the mix (laydown set) into fractioned mixes so that the quality, average of the characteristics, of each fractioned mix is as close as possible to the mixing quality.

The method revealed in this report basically aims to solve three problems: The variability among mixes, the variability among different sets of laydown and the variability within the laydown set in the opening line. As in this method the amount of bales used per pile varies at each laydown set, so each mix will have only a laydown set. Consequently this method presents a solution to the variability of mixing and variability in the distribution/laydown of bales within the laydown set in the opening line.

Functionality of the Method

Registration, Cotton Intake and Calculation of Inventory

1. The registration of the quantity of days which should be controlled the variability of quality among mixes.

2. Tolerance limit registration for each quality parameter among mixes.

3. Group of piles definition and association of each pile to a determined group of piles.

4. Mix Inventory calculation.

Mixing process comprises the steps:

Step 1—Quality planning for a given period.

Step 2—Prepare the premix.

Step 3—Generate mix (laydown set) from the premix.

Step 4—Minimum and maximum value calculation allowed in the mix.

Step 5—Inclusion of the bales which are at the "allocated bales" area.

Step 6—Search for the missing bales in inventory.

Step 7—Report bales either in spreadsheet or in a computer program.

Step 8—Select the bales of the mix (laydown set).

Step 9—Arrangement of bales in the opening.

Step 10—Separation of the selected bales for the mix and laydown into the production line.

First, the cotton inventory of each production line should be split into approximately 15 sectors denominated piles. The cotton inventory at plants often suffer from quality changes over time and to ensure homogeneity in the production process, so that changes in quality in the mixes are more gradual for each production line, the number of days should be informed so that the quality variation among the mixes can be controlled as well as the tolerance that each quality parameter allows to vary among mixes over the days of the quality control. As cotton arrives in the company, all the bales of the invoice are informed to the spreadsheets or a computer program and then stored in a single pile that is chosen by the user, preferably in the pile which has either been used less or has the same origin. After getting the quality of the bales of the invoice, the data are informed, and they are released for use in the mixes without the need of relocating the bales in inventory which precisely is the differential and then it characterizes the non-categorization of bales in the inventory. The piles—already qualified—compose the total inventory of each production line. For each production line, group of piles are created when it is set the percentage of use of each group of piles in the mix. Each pile is associated with a group of pile. Based on the percentage of all group of piles, the method calculates the inventory of the mix for each production line. From this stage on, the mixing process has started. The first stage is the quality planning for the following mixes of each production line, which has a defined duration in days by the user. By the means of the data of the mix in the process as well as the updated inventory data of the mix and number of days informed by the user, the quality to be produced in the forthcoming mixes is defined. The second stage of the mixing process is the definition of the premix. Due to the variability in the quality of the bales within each pile of the cotton inventory, a premix with approximately 50% more bales is prepared. For example, for a mix of 60 bales, a premix of 90 bales is composed. At this stage, based on the percentage in the mix for each group of piles, the quantity and quality of each pile, how many bales will be obtained from each pile to form the premix is set, in order to achieve the planned quality in the first stage. By the means of this premix methodology, which uses 50% more bales, both the best bales for the mix are chosen and full control is ensured with no categorization, which then reduces logistics and workforce (use of forklifts). It ultimately provides more uniformed quality of the mixes. At depot or at the cotton bale opening sector is created a premixing area hereafter denominated "Premix Area" where the bales are placed once picked for the premix. This area is divided into two parts, one in which the bales are stored from the previous mix denominated "allocated bales" and another where the bales are placed—obtained from piles—to complete the premix denominated "new bales". In the third stage, where the mix (laydown set) is carried out, the mix is created and then the minimum and maximum values of each quality parameter controlled in the mix are calculated; the left over bales from the previous mix are included; a report of the missing bales is generated; pick up in inventory the bales; which are taken to the premix "new bales" area. From the premix bales obtained, two thirds of the premix of the bales to form the new mix is chosen, according to the planned quality, the percentage of each group of piles and the minimum and maximum calculated value for each parameter. The remaining one third of the premix is kept to join the following premix. From the selected bales for the mix, the fourth stage of the mixing process takes place: the layout that indicates the position of each bale of the laydown set in the opening line is prepared, the mix is fractionated every eight bales, so that the fractioned mix has the same average quality of bales of the mix. After defining the arrangement of the bales in the opening line, coding labels are generated to be placed on each selected bale, identifying its position in the production line. The fifth stage starts when the bales are physically separated. The bales selected in the mix go to the production line and those not selected go to the "allocated bales" area which is kept to compose the next mix.

To better understand this descriptive report some merely illustrative—but not limited to—images were inserted.

FIG. 3 shows mix inventory calculation by the method.

Figure 1:
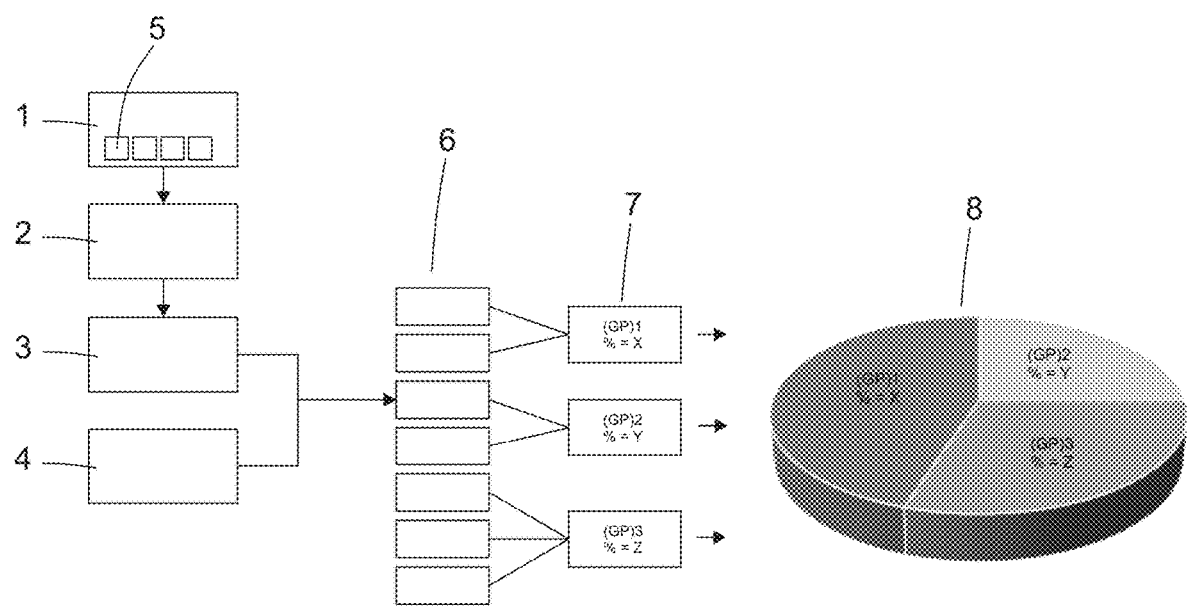
FIG. 1 shows briefly inlet flow of cotton in the inventory by the method.

As shown in FIG. 1, the inflow stream of cotton bales (5) comprises a truck fully loaded with bales (5) arriving at the factory. The cotton truck contains approximately 130 bales. Henceforth the truck is referred to as "invoice" (1). The second step comprises identifying (2) the bales (5) and withdrawing samples. The third step comprises storing (3) all the bales (5) of the invoice (1) in one of the piles (6) which has either been used less or has the same origin. The fourth step comprises informing (4) the quality data to either a spreadsheet or computer program and the bales (5) are released for use in the mix (8) with no need to separate them. The inventory is segmented into approximately 15 piles (6). The group of piles (7), with the respective percentages for the yarn manufacturing, comprises the mix inventory (8). The mix inventory (8) is segmented into approximately 15 piles (6) for each production line and when cotton arrives at the factory, all bales (5) of an invoice (1) are placed in a single pile even before being classified.

Figure 2:
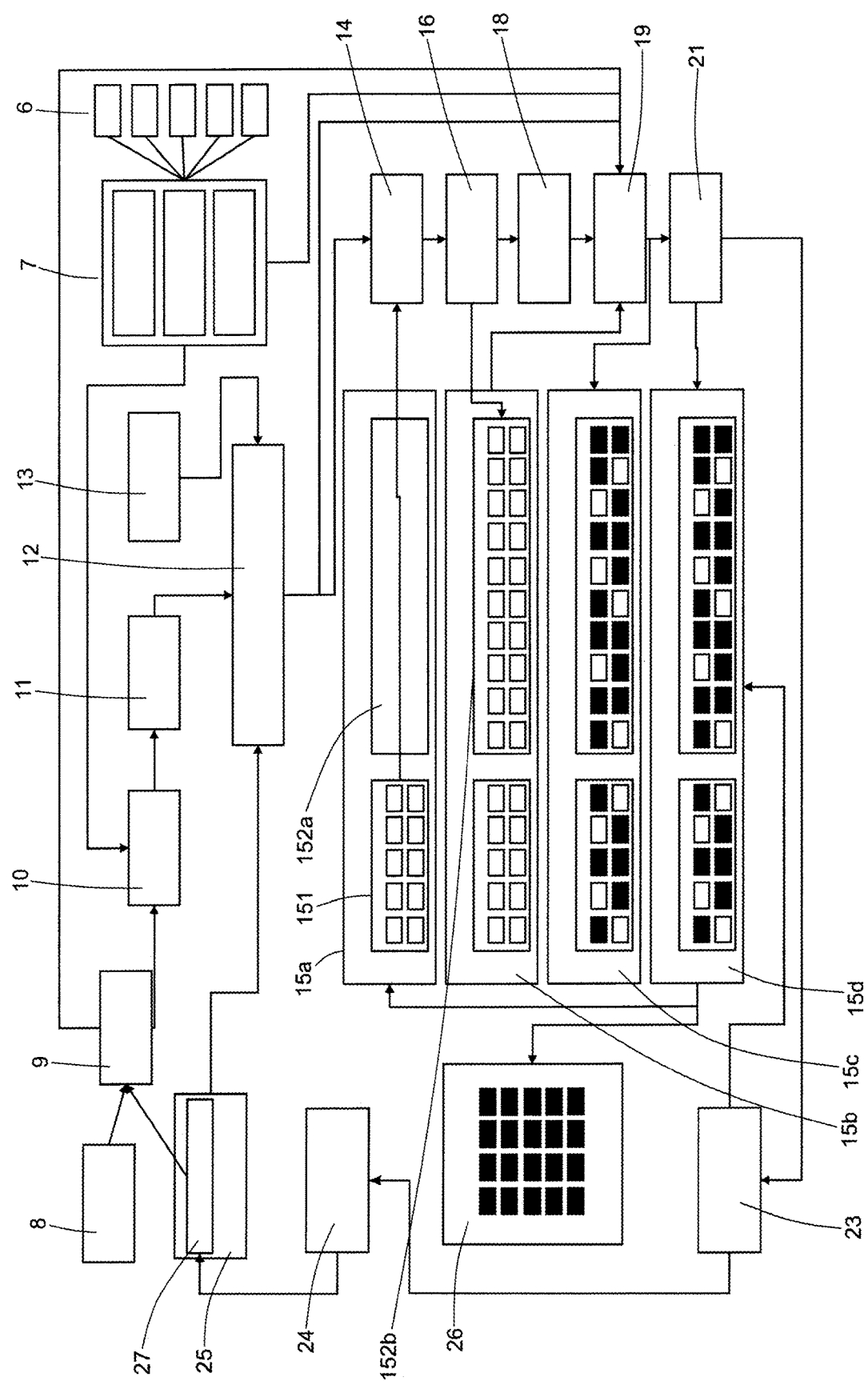
FIG. 2 shows briefly mixing process flow accomplished by the method.

As shown in FIG. 2, the flow of the mixing (24) process comprises the quality planning (9); the second step is the preparation of the premix (10) with 50% more bales (5); the third step is the creation of the new mix (11); the fourth step is the calculation (12) of the minimum and the maximum range of the mix (24), for each tolerance (13) of quality parameters and registered control days, this calculation takes into account the quality of the previous mixes (25); the fifth step comprises the inclusion (14) of the bales of the "Premix Area" (15a) containing the leftover from the previous mix (151). The "premix area" (15a) is divided into two parts, one where the remaining (151) bales of the previous mix are stored also referred to as "left over from the previous mix" and another part where the bales obtained from the piles (6) to complete the premix (15a) are denominated "New Bales" (152a). The sixth step picks up (16) the missing bales (5) from the piles (6) and places them at the "new bales" area (152b). On the seventh step the bale (5) codes that are at the "new bales" area (152b) are informed (18) to the spreadsheet or computer program. The eighth step selects (19) (15c) the bales (5) of the mix. The combination of bales is searched (19), which meets the requirements for the planned quality (9), the percentage of each group of piles (7) and the minimum and maximum calculated value (12) for each parameter in the mix. The selected bales (5) in this step are highlighted in the "premix area" (15c) by black rectangles. The ninth step fractions (21) the mix every eight bales (5), generates coding labels to be placed on each selected (15d) bale identifying its position in the production line (26). On the tenth step the bales (5) are separated (23) at the premix area (15d). In this separation (23) the bales (5) selected for the mix (24) are consumed in the opening line (26). The unselected bales (5) go to the premix area "leftover from the previous mix" (151) and the mix quality data (27) is stored in spreadsheets or in a computer program. Then the mix (24) is completed, the quality data of the mix (27) are taken into account for the definition of the quality (9) of the following mixes, and then the mixing flow process is reinitiated. In FIG. 2, the premix area shown at (15a), (15b), (15c) and (15d) corresponds to the same physical space in the warehouse, but in different situations: the area (15a) corresponds to the premix area with the left over bales from the previous mix (151) and the new bales area (152a) empty; the area (15b) corresponds to the premix area with the left over bales from the previous mix (151) and the area of new bales (152b) with the new bales which were picked up (16) from the piles of the inventory; the area (15c) corresponds to the premix area with the left over bales from the previous mix (151), now with the selected (19) bales for the new mix (24); In this example highlighted in black and the area of new bales (152b) with the new bales that were picked up (16) from the piles of the inventory, also with the selected (19) bales for the new mix (24); the area (15d) corresponds to the premix area with the left over bales from the previous mix (151), now with the indication (21) of the order of entry into the production line (26) for each of the selected (19) bales for the mix (24); In this example highlighted in black and the area of new bales (152b) with the new bales that were picked up (16) from the piles of the inventory, also with the indication (21) of the order of entry into the production line (26) for each of the selected (19) bales for the mix (24).

The Variability Among Mixes and the Variability Among Different Sets of Laydown

The variability among mixes and the variability among different sets of laydown are the main problem in cotton spinning, thus this method has a set of controls in order to decrease the variability among the mixes (24) and the variability among different sets of laydown (24) to the least possible ensuring no problems in the quality of cotton mixes (24).

The functionality of the method is described here through three topics: The Registration Process, Cotton Entry and Inventory Calculation, and the Mixing Process.

The Register, Cotton Entry and Inventory Calculation Process comprise:

1—Quantity of day registration in which the variability of quality among mixes (24) and the variability among different sets of laydown (24) should be controlled: the quantity of days per production line is informed so that the variation of each quality parameter among mixes (24) is controlled.

2—Tolerance registration for each quality parameter among mixes: The cotton inventory of plants often suffer from quality changes over time and to ensure homogeneity in the production process, so that changes in quality in the mixes (24) are more gradual for each production line it is registered for each quality parameter how much the average quality may vary (feature) and how much the average quality of each mix (24) may vary for a given period (days) (registered previously) among mixes of the production line.

3—Definition of group of piles (7): According to the quality of the piles (6) and the needs of each production line, one or more group of piles (7) is created. Each pile (6) of the inventory is associated to a group of pile (7). For each group of pile (7) is set the percentage of participation in the mix (% in the mix).

4—Mix inventory calculation (EM) (8): according to the group of piles (7) and their respective percentages the mix inventory (EM) (8) is calculated. For example, the worksheets below detail how the mix inventory calculation is done with regard to both quantity and quality.

Mixing Process Comprises the Steps:

Step 1—Quality planning of the mix: This step is the first stage of the mixes, where the quality of the next mixes is set. From available quality of the inventory (8) for the mix and quality (27) of the running mix, the quality (9) to be produced in the new mixes for the desired period is defined. In this step only the average quality of the mix inventory (8) is considered, since the average quality of each pile (6) and the individual quality of each bale (5) are considered only in steps 2 and 8 respectively.

Step 2—Preparation of premix: This step is the second stage of the mixing process. Due to variability in the quality of the bales (5) within each pile (6) of the cotton inventory, a premix (10) with approximately 50% more bales (5) is prepared, for example, for a mix of 60 bales, a premix (10) of 90 bales is composed. In the next step the best combination of bales (5) to the mix will be select and one third of the premix bales is discarded. The bales discarded remain in premix (15a) will participate in the selection of the following mix. With the premix (10) methodology—using 50% more bales (5)—selects the best bales for the mix, ensuring full control of quality in mixes with no need to categorize them, reducing logistics and workforce (use of forklifts). It provides a more uniformed quality of mixes. At this stage both the average quality mix inventory (8) and the average quality of each pile (6) are considered, since the individual quality of each bale (5) is only considered in step 8. Based on percentage in the mix of each group of piles (7), in the quantity and quality of each pile (6), how many bales (5) will be obtained from each pile (6) is defined, in order to achieve the planned quality.

Step 3—Generate mix: The third stage of the mixing process begins. From the premix (10) elaborated previously the new mix is generated (11).

Step 4—Minimum and maximum value calculation: After generating the mix, the minimum and maximum value (12) permitted for each quality parameter in the new mix are calculated, based on the previous mixes made (25), the quantity of days to be controlled and the tolerance variation registered (13) for each quality parameter among mixes.

Step 5—Inclusion of the bales which are at the "allocated bales" area: The allocated bales in the previous mix (151) which are at the "allocated bales" of the (Premix area) (15a) are included (14) into the new mix.

Step 6—Picking of the missing bales at inventory: In this step, the report of the missing bales (16) to complete the premix (10) is generated and then they are picked according to the amount defined per pile (6). These bales are laid down at the "new bales" (152a) of the premix (152b).

Step 7—Reporting the bales in a spreadsheet or computer program: After picking the missing bales at inventory, the code (18) of each bale (5) of the 'new bales' area (152b) is informed in order to obtain the quality data of the bale.

Step 8—Selection of the bales of the mix: This step completes the third stage of the mixing process. From the quality of each bale allocated in premix (15b), the bales that will compose the mix are selected (19) according to the mix percentage for each group of piles (7), and the quality for each parameter (characteristic) of the mix is between the minimum value and maximum value (12) previously calculated and is as close as possible to the planned quality (9) for the mixing.

Step 9—Bales laydown into production line (works with the variability inside the laydown set into production line):

To have a well-uniform distribution in the layout (map), after selecting the bales that will compose the mix (19), the distribution of bales for consumption in the production line is made. The mix is fractioned (group of 8 bales) (21), so that the quality of cotton of each fractioned mix (21) is as close as possible to the average quality of the mix.

Step 10—Separation of bales in the premix: After bale selection (19) and distribution/laydown in the production line (26), coding labels to be placed on each selected (15*d*) bale are generated, identifying its position in the production line (26), then the bales are physically separated—as in the attached example (FIG. 2)—in the pre-mixing area (15*d*); the selected bales go to the production line (26) and the non-selected ones go to the "allocated bales" area (151) of the premix area (15*a*).

The invention disclosed in this report allows cotton spinning mills to control in the mixes all import quality parameters to achieve greater uniformity in the yarn production. The method controls all the quality parameters of the mix without categorizing bales into class right after obtaining the quality data report. Consequently companies have reduction in logistics whenever managing bales by the means of forklifts and better optimization of spaces in the cotton inventory. The main benefit of this method is to provide total quality control in cotton mixes resulting in better efficiency of the producing machines and greater stability and uniformity of the produced yarn. With the implementation of this method reduction in defects is obtained, which can ensure the customer uniformed products and the quality of the cotton used within the limits considered ideal.

The worksheets below in FIG. 3 show the calculation formula and an example of the mix inventory per production line calculated according to the groups of piles. They show the definitions for quality tolerance control among mixes and an example of the calculation of the minimum and maximum value for the quality parameter in the mixing.

The invention claimed is:

1. Method for forming a homogenized mix of cotton bales for a spinning process where an inventory of said cotton bales have variable cotton fiber quality and where said cotton fiber quality data is specified on cotton bales contained in an inventory of cotton piles said method comprising the following steps:
    splitting said inventory of cotton piles into about 15 piles (6) to form a group of piles (7) which comprise a inventory mix (8);
    storing all the bales of a cotton lot (1) in a new pile (6) or in an existing pile having an identical origin;
    retrieving the quality data of the cotton bales (5) from the cotton lot (1), and transferring said quality data to spreadsheets or a computer program and thereafter releasing said quality data for use in processing said inventory mix (8);
    forming a total inventory of all of said 15 piles (6) that have the quality data of the said cotton bales (5) from the cotton lot;
    recording a number of days for which a that variation in quality among mixes (24) must be controlled;
    recording a tolerance (13) for each quality parameter among mixes;
    forming groups of piles and associate each of said 15 piles (6) to a particular group of piles;
    determine the components of the inventory mix (8);
    forming a homogenized mix of said inventory mix (8) as follows:
    Step 1—planning the quality (9) for a given period;
    Step 2—preparing a premix (10);
    Step 3—generating (11) a mix from the said premix (10);
    Step 4—calculating a minimum and maximum value (12) allowed in said mix;
    Step 5—including (14) remaining (151) bales of a previous mix;
    Step 6—taking (16) missing bales from inventory piles (152*a*) (152*b*);
    Step 7—recording (18) quantities of bales in the spreadsheet or computer program;
    Step 8—choosing (19) (15*c*) bales for the mix;
    Step 9—defining the positions (21) (15*d*) of bales of the mix to a production line;
    Step 10—separating (23) the identified bales for the mix and laydown into said production line (26).

2. Method for forming a homogenized mix of cotton bales for a spinning process according to claim 1, characterized by calculating the inventory mix {8} of cotton bales as follows:
    forming one group or more than one group of piles (7), where each pile (6) forming the inventory mix (8) is associated with a group of piles (7), and for each group of piles set the percentage in the mix;
    calculating the inventory mix (8) of cotton bales in quantity and quality, according to said one group of piles or more than one group of piles the respective percentages of said quality and quantity of said inventory mix.

3. Method for forming a homogenized mix of cotton bales for a spinning process according to claim 1, characterized by forming the premix (10) with 50% more bales based on quantity of mix (24) bales.

4. Method for forming a homogenized mix of cotton bales for a spinning process according to claim 3, characterized by placing 50% more cotton bales in the premix (10).

5. Method for forming a homogenized mix of cotton bales for a spinning process according to claim 3, characterized in that said premix is formed in a cotton depot, in a bale-opening area or a premix area denominated premix area (15*a*) where bales defined for the premix (10) will be laid down.

6. Method for forming a homogenized mix of cotton bales for a spinning process according to claim 3, characterized in that said premix area (15*a*) is split into two parts, one part where left over bales from a previous mix are stored and identified as allocated bales (151) and a second part where bales obtained from piles in order to complete a premix that is identified as new bales (152*a*) are laid down.

7. Method for forming a homogenized mix of cotton bales for a spinning process according to claim 1, characterized determining how many bales (5) will be obtained from each pile (6) to form the premix (10), based on a percentage in a mix of each group of piles (7), of a quantity and quality of each inventory of piles (6) and the planned (9) quality of a mix.

8. Method for forming a homogenized mix of cotton bales for a spinning process according to claim 1, characterized by calculating a minimum and a maximum (12) value for each quality parameter to be controlled in a mix, based on an average quality of previous mixes (25), according to the number of days on which production is to be controlled according a predetermined tolerance (13) for each quality parameter.

9. Method for forming a homogenized mix of cotton bales for a spinning process according to claim 1, characterized by adding (14) in the mix the bales which are at the allocated bales (151) area.

10. Method for forming a homogenized mix of cotton bales for a spinning process according to claim 1, characterized that cotton bales (16) are taken from inventory piles, according to missing bales of the premix and recording in a spreadsheet or computer program, in order to complete a premix (15*a*) of a new mix, according to an amount defined for each pile (6) in the preparation of the premix (10).

11. Method for forming a homogenized mix of cotton bales for a spinning process according to claim 10, characterized by taking bales (16) from inventory piles (6) and laying bales (5) down at a new bales area (152*a*) of the premix (15*a*) (152*b*).

12. Method for forming a homogenized mix of cotton bales for a spinning process according to claim 1, characterized by choosing (19) (15*c*) which bales (5) will compose a mix (24) according to the percentage in the mix for each group of piles (7) and an average quality of each parameter of the mix between the minimum and maximum values calculated (12) and too should be as close as possible to the quality planned (9) for the mix.

13. Method for forming a homogenized mix of cotton bales for a spinning process according to claim 12, characterized by after choosing (19) bales and the definition of the position (21) of the bales in the production line, bales are physically separated (23) in the premix area, and selected bales go to a production line (26) and the unselected bales go to an allocated bales (151) area.

* * * * *